US006583152B2

(12) United States Patent
Sosnowski et al.

(10) Patent No.: US 6,583,152 B2
(45) Date of Patent: Jun. 24, 2003

(54) COMPOSITION FOR REDUCING THE RISK OR PROGRESSION OF CARDIOVASCULAR DISEASES

(75) Inventors: Robert E. Sosnowski, Manasquan, NJ (US); Philip C. Lang, Toms River, NJ (US)

(73) Assignee: DexGen Pharmaceuticals, Inc., Manasquan, NJ (US)

( * ) Notice: Subject to any disclaimer, the term of this patent is extended or adjusted under 35 U.S.C. 154(b) by 0 days.

(21) Appl. No.: 09/845,141

(22) Filed: Apr. 30, 2001

(65) Prior Publication Data

US 2002/0164388 A1 Nov. 7, 2002

(51) Int. Cl.⁷ .................. A61K 31/44; A61K 31/50; A61K 31/495; A61K 31/78
(52) U.S. Cl. .................. 514/289; 514/284; 514/282; 514/249; 514/185; 424/195.1
(58) Field of Search .................. 514/289, 249, 514/185, 284, 282; 424/195.1

(56) References Cited

U.S. PATENT DOCUMENTS

| 5,866,585 A | | 2/1999 | Fogel |
| 5,922,773 A | | 7/1999 | Lipton et al. |
| 6,025,369 A | * | 2/2000 | Rosenquist et al. |
| 6,054,128 A | * | 4/2000 | Wakat |

FOREIGN PATENT DOCUMENTS

| WO | WO 00/37087 | * | 6/2000 |

OTHER PUBLICATIONS

Centrum references, Whitehall Robins: Centrum Focused Formulas Heart and Centrum Herbals Ginkgo, from www.centrum.com.*

Bucci, L. R., FDA filing reference, Aug. 27, 1999, pp. 1 and 2.*

*The Homocysteine Revolution* "A Bold New Approach to the Prevention of Heart Disease", Kilmer S. McCully, M.D., Keats Publishing, Los Angeles 1997, pp. 33, 92–93, 137, 181.

Bleich S., Degner, D., Bandelow, B., von Ahsen, N., Ruther, E., Kornhuber, J., *Plasma Homocysteine is a Predictor of Alcohol Withdrawal Seizures*, Neuroreport 2000, Aug. 21 Abstract.

* cited by examiner

Primary Examiner—Sreeni Padmanabhan
Assistant Examiner—S. Jiang
(74) Attorney, Agent, or Firm—DeLio & Peterson, LLC

(57) ABSTRACT

Elevated levels of homocysteine have been implicated as an important risk factor for cardiovascular and other diseases. A composition for decreasing levels of plasma homocysteine and a method for administering the composition are provided the composition containing dextromethorphan (DM), folic acid and vitamins $B_6$ and $B_{12}$. The composition provides a synergistic therapeutic effect so that lower amounts of the above ingredients may be employed to minimize any undesirable side effects caused by the use of high levels of a component such as DM. Preferred compositions for cardiovascular diseases further include lecithin, vitamin E, beta-carotene, procyanidins/flavonoids, trimethylglycine, garlic oil and minerals. Other compositions for treating glaucoma include bilberry, bioflavonoids and beta-carotene and for treating tardive dyskinesia include an antioxidant such as grape seed extract and pine bark extract, lecithin and oligomeric proanthocyanidins. The compositions may be administered using any suitable means such as orally or intravenous.

5 Claims, No Drawings

COMPOSITION FOR REDUCING THE RISK OR PROGRESSION OF CARDIOVASCULAR DISEASES

BACKGROUND OF THE INVENTION

1. Field of the Invention

The present invention relates to a composition and method for reducing the risk or progression of cardiovascular, glaucoma and tardive dyskinesia diseases and, more particularly, to a composition containing a number of ingredients which are present in amounts lower than amounts considered harmful to the body but which act synergistically to provide enhanced disease inhibition.

2. Description of Related Art

Cardiovascular disease is the most frequent cause of death in industrialized countries. Atherosclerosis (AS) is the principal cause of cardiovascular disease. AS is a disease of the intima of the arteries that leads to fatty lesions called artheromatous plaques on the inside surface of the arteries. This deposit of fat and cholesterol narrows the arteries, and often becomes calcified, providing sites for abnormal blood clots to form, leading to high blood pressure, heart attacks and strokes.

Elevated plasma homocysteine (Hcy) concentrations have repeatedly been associated with increased vascular risk. Hcy causes cells to decrease their production of clot preventing and clot dissolving substances and increases production of clot promoting substances. Hcy is an intermediate sulfhydryl alpha-amino acid formed during conversion of methionine to cysteine.

The buildup of Hcy in the body leads to overproduction of homocysteine thiolactone that causes low density lipoprotein (LDL) to become aggregated, and start to form plaque on the artery walls. Highly reactive oxygen radicals accumulate within this plaque resulting in damage to the lining cells of arteries, promoting blood clot formation and stimulating growth of arterial muscle cells which form fiberous tissue, mucoid matrix and degenerative elastic tissue (McCully K. *The Homocysteine Revolution,* Keats Publishers, Lincolnwood Ill.).

Thus, the presence of Hcy in the body has come to be a predictor of heart attacks, strokes, deep vein thrombosis and other circulatory problems. Evidence from The Life Extension Foundation indicates there is no "safe" normal range for Hcy. However, epidemiological data reveals that Hcy levels above 6.3 cause a steep progressive risk of heart attack. A method of lowering Hcy would prevent and/or inhibit these serious problems.

Dextromethorphan (DM) has recently been shown to decrease the levels of Hcy as discussed in U.S. Pat. No. 6,025,369. The amount of DM necessary to reduce Hcy to safe levels can cause undesirable side effects however.

Hcy and its degradation products are putative neurotransmitters and agonists at the N-methyl-D-aspartate (NMDA) receptor (*Neuroreport* 2000, August. 21; 11(12):2749–52). It has been shown that Hcy acts as an agonist at the glutamine binding side of the NMDA receptor (one type of excitatory amino acid receptor). Dextromethorphan (DM), a widely used OTC antitussive agent, is a noncompetitive antagonist of the NMDA receptor and is protective against the adverse effect of Hcy and its metabolites. DM, the d-isomer of the opiate agonist levorphanol, has none of the analgesic or sedative effects associated with the opiates. DM, acting as an antagonist at NMDA receptors, suppress the transmission of nerve impulses and nerve signals mediated through NMDA receptors. In addition, DM has also been reported to suppress activity at neuronal calcium channels.

Dextromethorphan and other NMDA receptor antagonists are known for treating glaucoma as discussed in U.S. Pat. No. 5,922,773 issued on Jul. 13, 1999 to Lipton et al. and for treating tardive dyskinesia as shown in U.S. Pat. No. 5,866,585 issued on Feb. 2, 1999 to Fogel. Both patents are hereby incorporated by reference.

Vitamin supplements of folic acid, $B_6$ and $B_{12}$ have been shown to be useful in lowering Hcy but there is evidence that for some elderly people it is not sufficient to keep the level of Hcy low enough to be out of the danger zone.

Bearing in mind the problems and deficiencies of the prior art, it is therefore an object of the present invention to provide a composition for reducing the risk or progression of cardiovascular diseases.

It is another object of the present invention to provide a composition for reducing the risk or progression of glaucoma.

A further object of the invention is to provide a composition for reducing the risk or progression of tardive dyskinesia disease.

It is yet another object of the present invention to provide a method for reducing the risk or progression of cardiovascular diseases in a person by administering to the person a composition of the invention.

Another object of the invention is to provide a method for reducing the risk or progression of glaucoma by administering to a person a composition according to the invention.

An additional object of the invention is to provide a method for reducing the risk or progression of tardive dyskinesia diseases by administering to a person a composition of the invention.

Still other objects and advantages of the invention will in part be obvious and will in part be apparent from the specification.

SUMMARY OF THE INVENTION

The above and other objects, which will be apparent to those skilled in art, are achieved in the present invention which is directed to a composition comprising a mixture of ingredients and a method for using the composition to reduce the risk or progression of cardiovascular, glaucoma and tardive dyskinesia diseases. The composition comprises a mixture of ingredients which act synergistically to provide the desired therapeutic effect. Broadly stated, levels of homocysteine are decreased in the plasma using known ingredients which are present in amounts below the amount which would cause harmful effects in the body yet still provide the desired therapeutic effects. Dextromethorphan (DM) in combination with folic acid, vitamin $B_6$ and vitamin $B_{12}$ are essential ingredients of the composition. Preferred compositions contain one or more of lecithin, vitamin E, beta-carotene, phytochemicals (e.g., proanthocyanidins, cyanidin, procyanidin, flavonoids, bioflavonoids), ginkgo biloba, trimethylglycine, garlic oil, vinpocetine, omega-3-oils, pantothenic acid, vitamin $B_3$, herbs such as kava and minerals, especially selenium, zinc, magnesium and calcium.

It is also preferred to employ in the composition a free radical inhibitor/antioxidant such as butylated hydroxytoluene (BHT) to protect the amino group in DM from oxidation and to provide a longer plasma level of DM.

In another aspect of the invention the composition may be used for preventing and/or treating glaucoma and damage to retinal ganglion cells using the composition of the invention further preferably including bilberry, bioflavonoids and beta-carotene and also oligomeric proanthocyanidins (OPC), vinpocetine and omega-3-oils.

In still another aspect of the invention the composition may be used for preventing and/or treating tardive dyskinesia using the composition of the invention further including antioxidants such as grape seed extract and pine bark extract, lecithin and oligomeric proanthocyanidins and also pantothenic acid, vitamin $B_3$, omega-3-oils and herbs such as kava.

In another aspect of the invention a method is provided for reducing the risk of or progression of cardiovascular, glaucoma and tardive dyskinesia diseases wherein the composition of the invention is administered by oral, sublingual, buccal, transdermal and intramuscular and intravenous means. Oral compositions may be formed into a soft-gel article, capsule, tablets, tablet with coating, sustained release or granular product.

DESCRIPTION OF THE PREFERRED EMBODIMENTS

The essence of this invention is to provide a composition containing a combination of ingredients which composition when administered to a person reduces the risk or progression of cardiovascular, glaucoma and tardive dyskinesia diseases by a synergistic action of the individual ingredients of the composition to lower Hcy levels in the body. Broadly stated, DM in combination with folic acid, vitamin $B_6$ and vitamin $B_{12}$ and preferably in combination with one or more of the following: lecithin (choline), phytochemicals, Vitamin A, preferably beta-carotene, vitamin E, ginkgo biloba, garlic oil, vinpocetine, omega-3-oils, pantothenic acid, vitamin $B_3$, herbs such as kava, trimethylglycine and minerals, provide such a therapeutic composition. The composition results in lowering of the Hcy in the blood without the side effects of using one or more or ingredients at levels which have adverse side effects in the body.

A N-methyl-D-aspartate antagonist is required in the composition as disclosed in U.S. Pat. No. 6,025,369 and of the disclosed antoginists dextromethorphan (DM) is the highly preferred ingredient in the composition of the invention. U.S. Pat. No. 6,025,369, supra, describes the action of DM to lower Hcy levels and the patent is hereby incorporated by reference. Side effects at high doses of DM include drowsiness, nausea and decreased coordination. Toxic high doses have also been described in the literature. DM in amounts of greater than 400 mg are considered to have undesirable side effects. In the composition of the invention DM in amounts of about 5 to 360 mg, preferably 30–120 mg in a single daily dose is preferred. The composition of the invention is typically taken once daily and the following ingredient amounts are based on a daily dosage.

With regard to the vitamins in the composition of the present invention, this will depend somewhat on the size, age, gender and health of the patient. Speaking generally, the vitamins will normally be from about 5% to about 2,000% of the RDA for that vitamin, most often from about 25% to about 1,000% of the RDA. Of course, the RDA can vary considerably with the factors illustrated above. Almost any accepted vitamin may be included in the present compositions, for example, vitamins A, D, E, K, thiamin, riboflavin, niacin, niacinamide ($B_3$), $B_6$, folate, $B_{12}$, biotin and pantothenic acid can all be included.

An inverse relationship has been observed between plasma folate and vitamin $B_{12}$ and plasma Hcy levels. Supplementation with these two vitamins leads to a significant decrease in Hcy levels. A significant decrease in the rate of the progression of carotid plaque in coronary heart disease patients has been reported with a supplement of 2.5 mg folate, 25 mg vitamin $B_6$ and 150 $\mu$g vitamin $B_{12}$ daily.

The essential vitamins in the composition are $B_6$, $B_{12}$, and folate, with vitamins E and A also being highly preferred.

The composition contains vitamin E at about 100 to about 600 IU, preferably 400 IU, vitamin $B_6$ at about 2 mg to about 100 mg, preferably 6 to 25 mg, folate at about 0.5 to about 10 mg, preferably 1 to 5 mg, and vitamin $B_{12}$ at about 0.01 to about 5 mg, preferably 0.1 to 3 mg.

Vitamin A precursors (provitamin A, carotenoids) can also be used including $\beta$-carotene, $\alpha$-carotene, cryptoxanthine and the like. The vitamin A esters and $\beta$-carotene are highly preferred forms of vitamin A. d-$\alpha$-Tocopherol and its esters are highly preferred as a source for vitamin E. Other sources of vitamin E include $\beta$-tocopherol, $\gamma$-tocopherol, the tocotrienols and their esters, tocopheryl nicotinate, and the like. Vitamin $B_6$ can be selected from hydrochloride salts or 5'-phosphates of pyridoxine, pyridoxamine or pyridoxal. The preferred vitamin $B_6$ is pyridoxine hydrochloride. The folate can be in the form of folic acid, mono and polyglutamyl folates, dihydro and tetrahydro folates, methyl and formyl folates. Folic acid is a highly preferred form of folate. Sources of vitamin $B_{12}$ are, for example, cyanocobalamin, methylcobalamin, adenosylcobalamin, hydroxocobalamin and the like. Cyanocobalamin is highly preferred.

Vitamin A, preferably Beta-carotene, is employed at about 5,000 to 25,000 IU, preferably 10,000 to 25,000 IU.

Evidence suggests that lecithin reduces the risk of cardiovascular diseases by inhibiting intestinal absorption of cholesterol and bile acids and favorably affecting lipoprotein levels. Fatty deposits containing cholesterol which thicken the arterial walls cause atherosclerosis, or hardening of the arteries. Lecithin, an emulsifier, helps clear the arteries of these deposits. Lecithin also demonstrates antioxidant activities, preventing free radical damage in the arteries. Lecithin and the choline component of lecithin, play a number of roles in cardiac function. Choline participates in the metabolism of Hcy. Choline or lecithin can reduce Hcy levels and it has been reported that like folic acid, choline is involved in metabolizing Hcy and has been shown to be partially effective in lowering Hcy in humans. The disease tardive dyskinesia, associated with a malfunction of cholinergic nerve transmission has been reported to be treatable with lecithin, a source of choline. Lecithin may be employed in an amount of 300 to 2500 mg, preferably 600 to 1800 mg and it is preferred that lecithin be used rather than choline.

The herb Ginkgo biloba is a preferred ingredient in the composition because it has been shown to help prevent and treat stroke and heart disease. Its properties include antioxidant, anti-inflammatory and a toner of blood vessels. Other herbs such as kava are also preferred for use in the composition. Amounts of about 20 to 200 mg, preferably 40 to 120 mg, are used.

Garlic oil is used in the composition because of its known ability to lower cholesterol, lower high blood pressure and aid in improving circulation. An amount of 50 to 500 mg, preferably 100 to 400 mg, may be employed.

Trimethylglycine may be used in amounts of 50 to 1,000 mg, preferably 100 to 500 mg and is useful in the methylation of homocysteine.

The mineral supplement component of the compositions of the present invention comprises sources selected from calcium, phosphorus, magnesium, iron, zinc, iodine, selenium, copper, manganese, fluoride, chromium, molybdenum, potassium, and chloride, preferably selenium, zinc, magnesium and calcium. The mineral sources are preferably present in an amount of at least 10% of the RDA of these minerals, and more preferably, at least 30% of the RDA per unit dose of the finished composition.

The amount of the above minerals in the composition is for calcium 200 to 1500 mg, preferably 400 to 800 mg; magnesium 100 to 500 mg, preferably 200 to 400 mg; zinc 10 to 100 mg, preferably 15 to 50 mg; and for selenium 50 to 200 µg, preferably 100 to 200 µg.

The source of the mineral salt can be any of the well known salts including carbonate, oxide, hydroxide, chloride, sulfate, phosphate, gluconate, lactate, fumarate, citrate, malate, amino acids and the like for the cationic minerals and potassium, calcium, magnesium and the like for the anionic minerals.

As discussed in U.S. Pat. No. 6,025,369, supra, the basis of that patent is that the gross effects of homocysteine on vascular smooth muscle cells is mediated through a NMDA-like glutamate gated calcium ion channel receptor. Based on this finding the growth effects of homocysteine can be blocked through the use of NMDA receptive antagonists.

Thus, the invention in the '369 patent comprises a new class of drugs for treating and prevention of atherosclerosis and these drugs act to inhibit the cell biochemical physiological actions of homocysteine activated homocysteine receptor. One class of drugs which effectively accomplish this objective includes those which are NMDA receptor blockers.

A number of NMDA receptor blockers are cited in the patent and the preferred compound are the morphinans which include dextromethorphan which has the general formula:

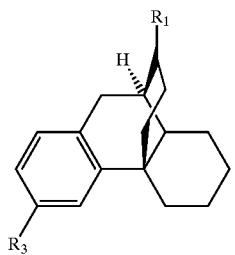

In the preferred embodiment, dextromethorphan, $R_1$ is methyl, $R_3$ is methoxy. For dextrorphan $R_3$ is hydroxy.

While other of the NMDA antagonists as noted in the Rosenquist et al. '369 patent and in the Lipton et al. and Fogel patents, supra, may be used, DM is preferred. Any other NMDA receptor antagonists may be used and other compounds include amantadine derivatives (e.g., memantine, amantadine and rimantadine).

The present composition also preferably contains a combination of botanical compounds, e.g., phytochemicals, in amounts of about 20 to 500 mg, preferably 50 to 300 mg.

Phytochemicals may be broadly defined as chemicals derived from plants and include plant sterols, flavonoids and sulfur containing compounds. Plant sterols include sitosterol, stigmasterol and campestrol. Flavonoids are compounds with varied chemical structures present in fruits, vegetables, nuts and seeds. The major flavonoid categories are flavonoids, flavones, catechins, flavonones and anthocyanidins. Naturally occurring sulfur compounds (the allium family) are found in garlic, onions and leeks.

Flavonoids is a generic term for a group of aromatic oxygen heterocyclic compounds derived from 2-phenylbenzopyran or its 2,3-dehydro derivative. They are widely distributed in higher plants and the subgroup is the anthocyanidins. Another subgroup, referred to as Vitamin P activity, are called bioflavonoids and high concentrations can be obtained from citrus fruits.

Bioflavonoids, obtained from a variety of plant extracts, have been shown to exhibit antioxidant activity and to improve cardiac function.

Proanthocycanidins are often called condensed tannins and are found in plants and are generally oligomers or polymers of flavonoid units (e.g., flavan-3-ol) linked by carbon-carbon bonds not susceptible to cleavage by hydrolysis. The most common anthocyanidins are cyanidin (flavan-3-ol, from procyanidin) and delphinidin (from prodelphinidin). Proanthocyanidins normally contain 2 to 50 or greater flavonoid units.

Phytochemicals included in the present compositions include bioflavonoids, such as for example, mono-acetyl-vitexinrhamnoside, rutin, luteolin-7-glucoside, hyperoside, and preferably quercetin and/or catechin. Preferably, the composition of the present invention contain combinations of various flavonoids such as catechin and/or quercetin. The bioflavonoids can be added to the present composition in purified form or as part of a plant or other extract, for example. Amounts of about 5 to 500 mg, preferably 10 to 100 mg are used, especially in the glaucoma compositions.

Oligomeric proanthocyanidins (OPC) type of procyanidins (a type of flavonoid from grape seed extract or pine bark extract) have been shown to reduce platelet aggregation, to prevent free radical damage in the arteries and the brain, and to treat tardive dyskinesia (for which there are no effective drugs). Vitamin E and beta-carotene are known antioxidants which are added to the composition of our invention to prevent free radical damage to the arteries and to prevent lipid peroxidation. An amount of OPC is used at about 10 to 300 mg, preferably 50 to 100 mg, especially for the glaucoma and tardive dyskinesia compositions.

Bilberry is an antioxidant and is used especially in the glaucoma composition in an amount of about 10 to 200 mg, preferably 20 to 120 mg.

The phytochemical component of the composition of the present invention may also include at least one of procyanidin or cyanidin and preferably, contains a mixture of procyanidin and cyanidin. These phytochemicals have an antioxidant effect and have been demonstrated to protect vascular endothelial cells from oxidant injury. The procyanidin and cyanidin component of the present composition may be added as a mixture of both compounds or each may be added separately, in purified form or as an extract. In a preferred embodiment, procyanidin and cyanidin are added as a mixture and most preferably are obtained as an extract from grape seed, pine bark or other plant containing sufficient amounts of these compounds. Amounts of 10 to 300 mg, preferably 50 to 150 mg are used.

Herbs useful in the compositions of the invention include kava and may be used in amounts of 10 to 500 mg, preferably 40 to 200 mg.

In the glaucoma composition bilberry, bioflavonoids, beta-carotene and oligomeric proanthocyanidins are preferably included in the above composition. Other components include vinpocetine in an amount of about 1 to 10 mg, preferably 2.5 to 5 mg. Omega-3-oils, such as fish oil are also preferred in amounts of about 0.1 to 4 g, preferably 0.5 to 2 g.

In the tardive dyskinesia composition an antioxidant such as grape seed extract and/or pine bark extract, lecithin and oligomeric proanthocyanidins and herbs are preferably added to the above composition. Other components include panthothenic acid in an amount of about 5 to 250 mg, preferably 10 to 50 mg, a herb such as kava in an amount of about 10 to 100 mg, preferably 25 to 70 mg, vitamin $B_3$ in an amount of about 10 to 100, preferably 20 to 50 mg, and omega-3-oils in an amount of about 0.1 to 4 g, preferably 0.5 to 2 g. Kavalactone is the active chemical in kava.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A composition for lowering homocysteine levels in the body consisting essentially of:
   dextromethorphan;
   folic acid or folate;
   vitamin $B_6$; and
   vitamin $B_{12}$.

2. A composition for lowering homocysteine levels in the body consisting essentially of:
   dextromethorphan;
   folic acid or folate;
   vitamin $B_6$;
   vitamin $B_{12}$;
   lecithin; and
   vitamin E.

3. A composition for lowering homocysteine levels in the body consisting essentially of:
   dextromethorphan;
   folic acid or folate;
   vitamin $B_6$;
   vitamin $B_{12}$
   lecithin;
   vitamin E; and
   beta-carotene.

4. A composition for lowering the homocysteine levels in the body consisting essentially of in a daily dose:
   dextromethorphan in an amount of about 5 to 360 mg;
   folic acid or folate in an amount of about 0.5 to 5–10 mg;
   vitamin $B_6$ in an amount of about 2 to 100 mg; and
   vitamin $B_{12}$ in an amount of about 0.01 to 5 mg.

5. The composition of claim 4 consisting essentially of in a daily dose:
   dextromethorphan in an amount of about 30 to 120 mg;
   folic acid or folate in an amount of about 1 to 5 mg;
   vitamin $B_6$ in an amount of about 6 to 25 mg; and
   vitamin $B_{12}$ in an amount of about 0.1 to 3 mg.

* * * * *